United States Patent [19]

Holtman

[11] Patent Number: 4,685,914
[45] Date of Patent: Aug. 11, 1987

[54] DISPOSABLE URINARY PAD

[75] Inventor: Dennis C. Holtman, Flemington, N.J.

[73] Assignee: Personal Products Company, Milltown, N.J.

[21] Appl. No.: 764,701

[22] Filed: Aug. 12, 1985

Related U.S. Application Data

[63] Continuation-in-part of Ser. No. 746,600, Jun. 19, 1985, abandoned, which is a continuation-in-part of Ser. No. 535,193, Sep. 23, 1983, abandoned.

[51] Int. Cl.⁴ ............................................. A61F 13/16
[52] U.S. Cl. .................................... 604/368; 604/369; 604/385 R; 604/378; 604/367
[58] Field of Search ............... 604/379, 380, 360, 366, 604/369, 370, 374, 376, 385, 368, 367

[56] References Cited

U.S. PATENT DOCUMENTS

| | | | |
|---|---|---|---|
| 2,069,092 | 1/1937 | Jackson | 604/397 |
| 3,525,337 | 8/1970 | Simons et al. | 604/374 |
| 3,805,790 | 4/1974 | Kaczmarzyk et al. | 604/387 |
| 4,372,312 | 2/1983 | Fendler et al. | 604/370 |

Primary Examiner—C. Fred Rosenbaum
Assistant Examiner—Sherri E. Vinyard

[57] ABSTRACT

The invention provides a disposable urinary pad having high liquid impact capacity, high liquid retention, and allows the skin of the wearer to remain dry. The pad is comprised of a liquid-impermeable, substantially flexible shell containing a fibrous web superstructure substantially filling the shell and an absorbent medium between the superstructure and the bottom of the shell.

30 Claims, 8 Drawing Figures

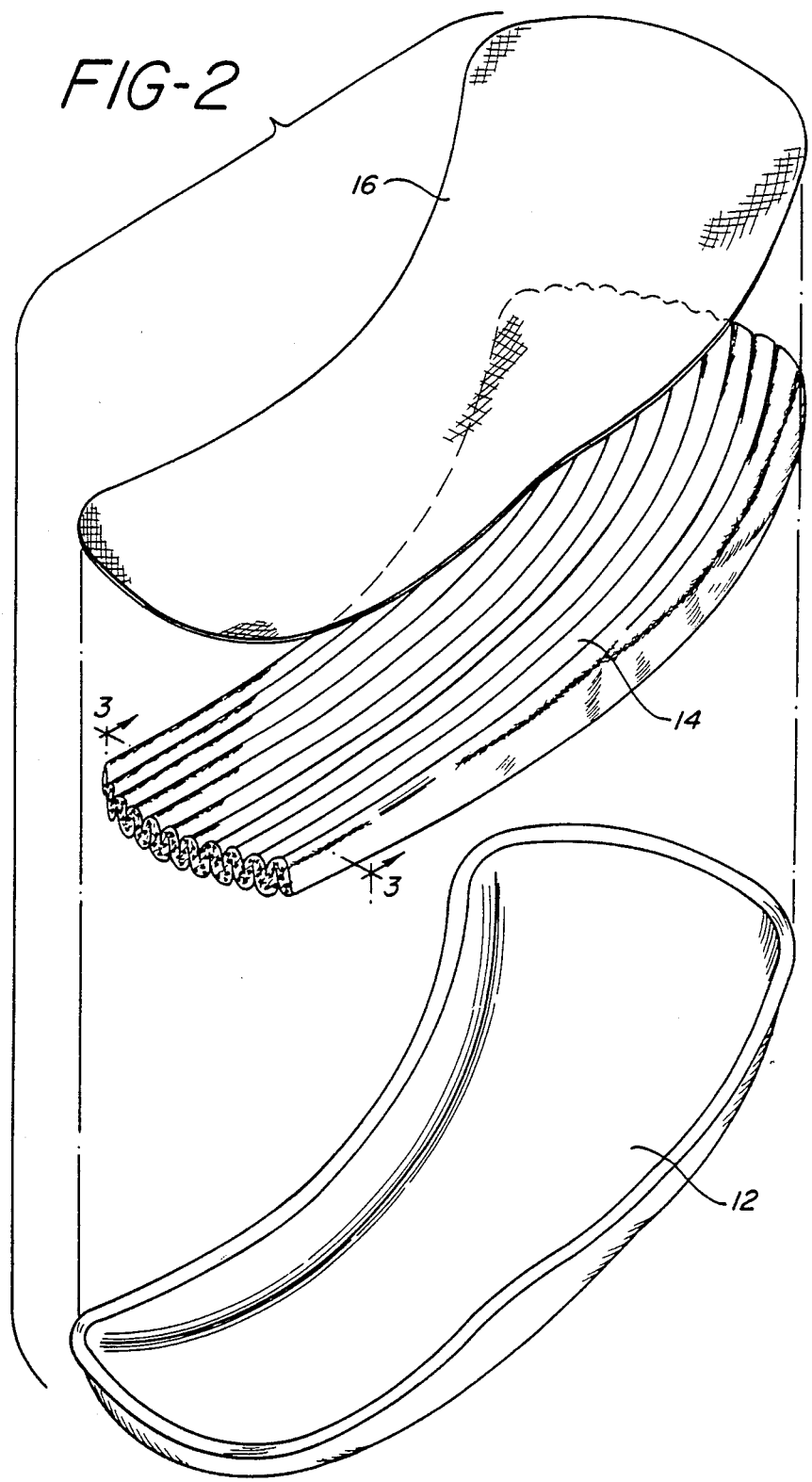

DISPOSABLE URINARY PAD

This is a continuation-in-part of copending application Ser. No. 746,600, filed June 19, 1985, which application is a continuation-in-part of application Ser. No. 535,193 filed Sept. 23, 1983, both now abandoned.

BACKGROUND OF THE INVENTION

The present invention relates to a new and improved disposable urinary pad having high liquid impact capacity, high liquid retention, and allows the skin of the wearer to remain dry.

Disposable absorbent products have been known for some time, including such products as disposable diapers, sanitary napkins, wound dressings, bandages, incontinent pads, and the like. These products incorporate an absorbent batt which is used to absorb and hold or contain body fluids. Initially in many of these products, especially diapers and sanitary napkins, the absorbent batt comprised what is termed "wadding" or plies of tissue. The wadding was disposed between a liquid-impermeable backing and a liquid-permeable facing and the plies of tissue were used to absorb and, hopefully, contain the liquid within the product. A diaper which utilizes such an absorbent batt is disclosed in U.S. Reissue Pat. No. 26,151.

The wadding type of product was replaced, for the most part, by an improved absorbent batt which comprises what is termed "fluffed wood pulp fibers". This absorbent batt comprises a layer of individualized wood pulp fibers with the layer having substantial thickness. A diaper which incorporates such fluffed wood pulp absorbent batt is described in U.S. Pat. No. 2,788,003. This diaper had improved absorbent capacity and somewhat better containment than a diaper using a wadding layer. Also, the fluffed wood pulp layer is quite soft, flexible, and conformable, and, hence, produces an improved diaper over diapers using wadding as the absorbent layer.

Though the fluffed wood pulp absorbent batts have improved capacity, the efficiency with which the capacity is sued in a diaper or sanitary napkin is poor. The reason for this is that the fluid to be absorbed is generally deposited in a localized area within the absorbent batt, and the ability of the fluid to move along the plane of the batt is poor. The fluid tends to follow a radial wicking path and consequently moves to the closest edge of the batt where it generally is no longer contained and the product leaks.

U.S. Pat. No. 3,017,304 discloses an absorbent product which incorporates in the product a densified paper-like layer. This paper-like layer acts as a wick i.e., liquid which is placed on the layer tends to move rapidly along the plane of the layer. When incorporated in combination with fluffed wood pulp fiber, the resultant product uses the absorbent capacity of the fluffed wood pulp much more efficiently. Diapers which incorporate this paper-like layer combined with fluffed wood pulp are disclosed and described in U.S. Pat. Nos. 3,612,055 and 3,938,522. This concept of combining wicking ability, or a capillary skin or layer, with fluffed wood pulp fibers has gained wide acceptance in many absorbent products including disposable diapers and sanitary napkins. Even though these products make much greater use of the capacity of the absorbent batt, they still do not totally contain the absorbed liquid. It is probable that these products will leak before the full capacity of the batt is used for the absorption or, at the very least, before the entire liquid void by the user is absorbed. This is especially true when pressure is placed on the batt while wet. For example, a baby sitting down on a previously wetted diaper will very often cause the batt to leak.

An incontinent adult faces not only the problems of the infant but many other problems. First, the void of an adult generally is much higher in volume than that of an infant. Second, a bulge under clothing is accepted by society for an infant, but the ambulatory adult with an incontinence problem longs for a product which is not visible through ordinary clothing. Third, the proportions and shape of the legs and torso of the adult differs considerably from those of an infant. Therefore, a mere enlargement of an infant diaper, such as that shown in U.S. Pat. No. 4,253,461, is not a satisfactory product.

In both the infant diaper and adult incontinent product marketplace, a product is needed which has a large storage capacity. For instance, shaped containers have been suggested. However, these containers have been substantially rigid, do not stay in place, and are quite uncomfortable. A product with a substantially large storage capacity, with an ability to move liquid away from the void zone, which is disposable, which is comfortable, and which does not show through wearing apparel is needed in the marketplace.

A number of years ago, "superabsorbent materials", i.e., materials which will absorb many times their weight of liquid, were developed. Since the development of such materials, attempts to incorporate them in absorbent products such as diapers to enhance the absorption performance of these products have been made. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a permeable facing and an impermeable backing sheet. The absorbent layer contains water-insoluble cross-linked hydrocolloid polymer as the superabsorbent material.

Even though superabsorbent materials have been available for some time, they have not gained wide acceptance in absorbent products such as disposable diapers, and sanitary napkins. A primary reason for this lack of acceptance of superabsorbents is failure to develop a product capable of economically utilizing the highly increased absorptive capacity of the superabsorbent material. In order to economically utilize a superabsorbent, the liquid being absorbed must be readily accepted and placed in contact with the superabsorbent material. Furthermore, as the superabsorbent material absorbs liquid, it must be allowed to swell. If the superabsorbent is prevented from swelling, it will cease absorbing liquid. Hence, if the superabsorbent material is to function in absorbent products, such as diapers and sanitary napkins, wherein the liquid to be absorbed is placed in a small void area, the structure of the absorbent layer containing superabsorbent materials must have certain characteristics. Over the years a number of techniques have been disclosed in an attempt to provide structures which make efficient use of the superabsorbent material. Such products are disclosed in U.S. Pat. Nos. 4,103,062, 4,102,340, and 4,235,237. In addition, methods for incorporating superabsorbents into suitable layers or suitable configurations which can be placed in an absorbent product, are disclosed in U.S. Pat. Nos. 4,186,165, 4,340,057 and 4,364,992. To date, none of these products has met with any substantial commercial success.

The present invention provides a new and improved absorbent product which possesses a large storage capacity, which is soft and comfortable, which can be designed so as not to be apparent through normal clothing and which utilizes a substantial portion of the absorptive capacity of superabsorbent materials. In addition, the new absorbent product will contain absorbed liquid even when pressure is placed upon the product during use.

SUMMARY OF THE INVENTION

The present invention provides a disposable urinary pad which comprises a liquid-impermeable substantially flexible shell containing a fibrous web superstructure, capable of a substantial transverse post-compression recovery, and an absorbent medium.

The shell is formed from a moldable substance which is liquid-impermeable. For example, the shell may be a polyethylene foam shell which is formed from a blown polyethylene foam sheet, subsequently subjected to molding by a thermal process. The shell generally has a boat-like shape and ranges in thickness from about 1/64 inch to about ¼ inch in thickness. The shell has a length which ranges from about 4 inches to about 12 inches, a width measured from one rim to another across the top space from about 2 inches to about 7 inches, and a depth, measured from a line extending across the width at the upper shell rim in the central portion to the bottom of the shell interior, from about 0.5 to about 2.5 inches.

The superstructure which is placed in the shell and substantially fills (i.e., at least 40%) the shell is at least slightly compressible and has a transverse post-compression recovery of at least 80%, preferably 90%, when wet. The superstructure is comprised of hydrophobic, wet resilient, dry resilient fibers in web form. The superstructure is non-collapsible from the weight of liquid when wet and, hence, is able to accept a liquid void even after having been wetted previously and after compression restores substantially its original configuration thereby providing excellent stability. Furthermore, the superstructure is characterized by allowing at least about 20 cc/second of liquid to pass through the fibrous web. In one embodiment, a fibrous nonwoven web is formed of a resilient fiber such as polyester. The web is corrugated and stabilized to prevent the corrugations from separating or flattening when the web is wet and has pressure placed upon it.

The absorbent medium is superabsorbent material, hydrophilic fibers which are loosely compacted or formed into a nonwoven web, wadding tissue, peat moss, mixtures thereof or the like.

In a specific embodiment of the present invention, a liquid-permeable fabric or web covers the side of the shell which is open. This cover or facing is sealed to the rim of the shell thereby entrapping the superstructure and the absorbent medium which have been placed in the shell. If the urinary pad does not have a facing or covering, the superstructure, and if necessary, the absorbent medium, are affixed to the shell so as to remain in position even when wet.

The product of the present invention has a high impact capacity i.e., the product accepts a relatively large quantity of liquid quickly and retains it. Furthermore, the product does not leak or spill over. In other words, once the urine enters the pad, the urine remains entrapped within the product. The product also has a high liquid-holding capacity. In addition, the product maintains its surface dry thereby keeping any moisture away from the skin of the wearer. Still further, the product of the present invention permits air circulation in the region where the product is worn which results in a high degree of comfort.

BRIEF DESCRIPTION OF THE DRAWINGS

FIG. 2 is a perspective view of the parts prior to assembly which provide one embodiment of the present invention;

DETAILED DESCRIPTION OF THE INVENTION

Figure 1:
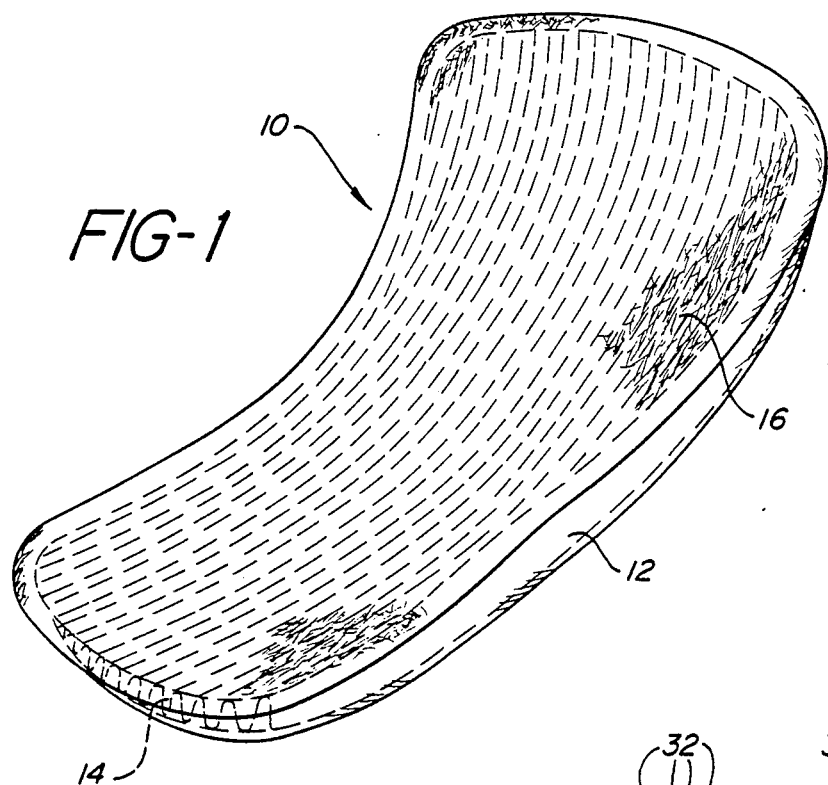
FIG. 1 is a perspective view of one embodiment of the present invention.

FIG. 1 depicts a perspective view of a disposable urinary pad 10 which has a polyethylene-containing foam shell 12 containing a corrugated fibrous web 14 and has a facing 16 sealed to the rim of the shell 12.

FIG. 2 illustrates the same urinary pad 10 from FIG. 1 with the elements separated and showing their relationship. The shell 12 is a polyethylene-containing foam shell which is preformed by a thermal molding process known in the art. The shell is about 1/16 inch thick and is boat-shaped. The top of the shell rims are at least ½ inch in depth from the bottommost point of the shell interior. On the underside of the shell 12 are adhesive lines which are applied to provide the securement means for securing the urinary pad to the clothing of the user. These adhesive lines are covered with release strips which, when peeled from the adhesive strips, leave the adhesive tacky. The superstructure 14 is a corrugated fibrous web which generally is at least ½ inch thick and contains about four or five corrugations per inch. In a specific embodiment, a polyester fibrous web is carded which web has a basis weight of about 25 grams per sguare meter. The web is corrugated, in other words, transversely folded, by known procedures such as that exemplified in U.S. Pat. No. 4,111,733, preferably, the web is stabilized so that when the web becomes wet it does not lose its corrugated configuration. In this embodiment, the absorbent medium (not shown) is affixed to the corrugated web as small particles or film-like partial coverings of the web fibers. The facing 16 is a liquid-permeable, generally hydrophobic fibrous web which may have a typical weight basis of 0.5 oz/yd². The three elements, the shell 12, the absorbent structure 14, and the facing 16, are combined as shown in the drawing, the facing being sealed at its edge to the rim of the shell so as to provide a unitary product.

Figure 3:
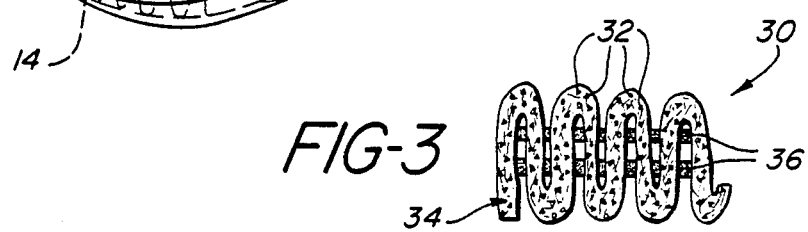
FIG. 3 is a cross-sectional view taken through lines 3—3 of FIG. 2.

FIG. 3 is a cross-sectional view along line 3—3 of FIG. 2 of a portion of a typical corrugated web. This portion 30 of the web shows the web 34 in a corrugated form wherein superabsorbent 32 has been placed among the fibers of the web. The web has been stabilized by thermal bonding of fusible fibers 36 which are in the blend of fibers forming the web 34.

Figures 4, 5:
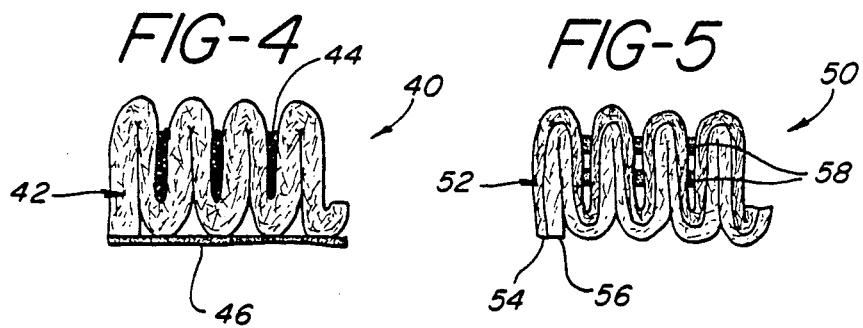
FIG. 4 is a cross-sectional view, like FIG. 3, of another embodiment of the present invention.
FIG. 5 is a cross-sectional view, like FIGS. 3 and 4, of still another embodiment of the invention.

FIG. 4 shows a cross-sectional view of another portion 40 of another corrugated web 42 suitable for use in the present invention. The corrugated web 42 is a fibrous web but does not contain any superabsorbent within the web fibers. Instead, the superabsorbent 44 is placed between the corrugation folds of the web. Thus, as the web accepts and retains a void volume of liquid, the liquid is readily in contact with the superabsorbent. The corrugated web 42 is stabilized by the thin coating of adhesive 46 placed on one side of the corrugated web 42. The corrugated web 42 would be placed in the urinary pad of the present invention with the open corrugations toward the facing surface.

FIG. 5 is a cross-sectional view of still another portion 50 of a corrugated web 52. This corrugated web 52 contains two layers 54 and 56. The layer 54 is a fibrous layer of hydrophobic fibers which layer has a lower capillary pressure than the second layer 56. The corrugated web 52 is stabilized by fusible fibers 58. When the web is exposed to a temperature which substantially melts these fibers, the corrugations in the web are partially fused together.

Figure 6:
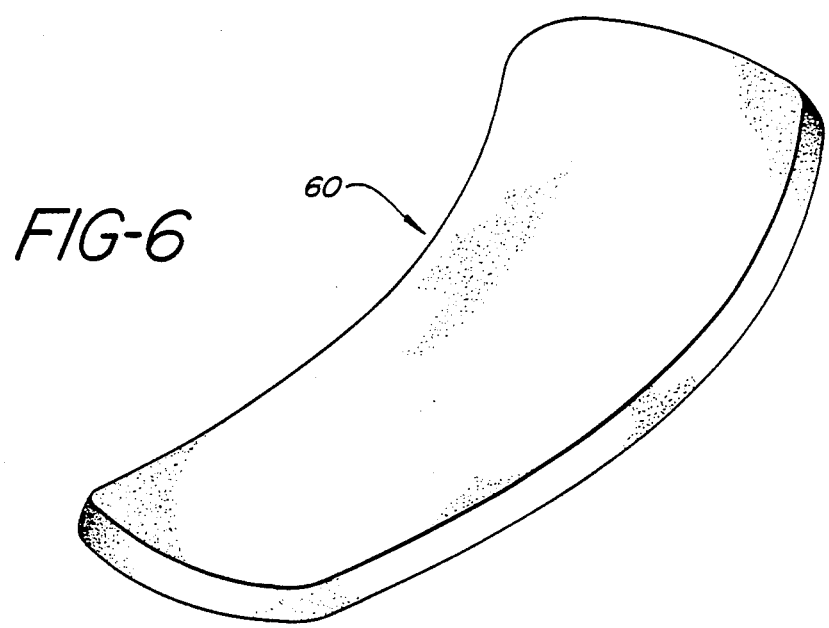
FIG. 6 is a perspective view of one element of a specific embodiment of the present invention.

FIG. 6 depicts an open cell foam 60 substantially rectangular in shape, which can be placed in the shell of the urinary pad of the present invention.

Figure 7:
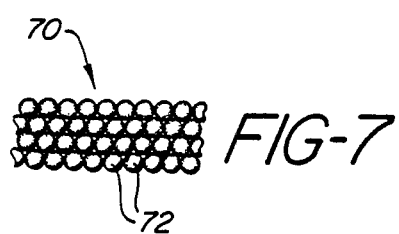
FIG. 7 is a cross-sectional view of a fragment of one element of a further embodiment of the present invention.

FIG. 7 is a cross-sectional view of a fraction 70 of styrofoam beads 72 which form the superstructure placed in the shell of the urinary pad of the present invention. These styrofoam beads 72 are placed in the shell so as to substantially fill the shell.

Figure 8:
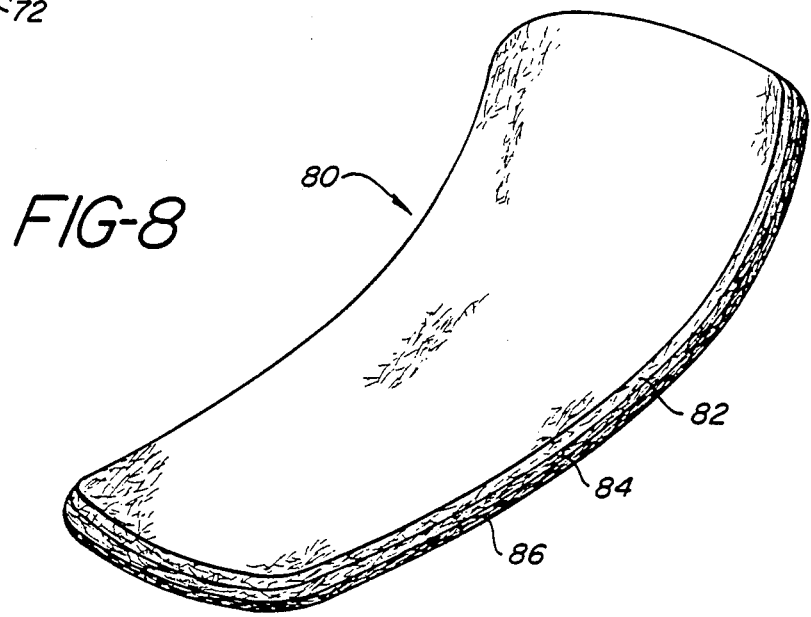
FIG. 8 is a perspective view of one element of a still further embodiment of the present invention.

FIG. 8 depicts a multilayer web structure 80 wherein the first layer 82 is of a lower density than is the second layer 84, and the second layer 84 is of a lower density than is the third layer 86. This multilayer fibrous web 80 would be placed in the shell so that the first fibrous layer 82 is in contact with the facing. These and other products, such as a rectangular incontinent pad, or a smaller urinary pad for a young child or possibly an infant, may be made along the same lines as the products depicted in FIGS. 1-8.

The liquid-impermeable substantially flexible shell is formed from a moldable substance. The substance, when molded, should provide a liquid-impermeable substantially flexible shell with a thickness ranging from about 1/64 inch to about ¼ inch. The shell, when deformed, should substantially return to its original shape. Substances which provide these characteristics and which are moldable by pressure, or thermal molding, or the like are suitable. Particularly suitable for use in the present invention is an ethylene-containing polymer foam.

The ethylene-containing polymer foam shell is prepared by known thermal molding processing. One preferred formulation for forming the ethylene-containing polymer foam material is identified as Volara Type A, which is a crosslinked polyethylene foam. The product is manufactured and sold by Voltek, Inc., Lawrence, Mass. The expression "ethylene-containing polymer foam" used herein includes polyethylene homopolymer and ethylene-containing copolymers, preferably containing a major portion, by weight, of ethylene. It is preferred that the polymer present be crosslinked. Preferred comonomers, for preparing the polymers, include vinyl acetate, acrylic and methylacrylic acids and esters, such as ethyl acrylate. Blends of such polymers can also be used. Preferably, the formulation is prepared in sheet form at approximately ⅛ inch in thickness. The sheet is subjected to thermal molding at a temperature of about 260° F. to form the foam shell. The shell is boat-like in shape, but is not limited thereto. The length of the shell ranges from about 4 inches to about 12 inches, with a width from about 2 inches to about 7 inches. The thickness of the shell ranges from about 1/64 inch to about ¼ inch. The depth of the shell is measured by extending a line horizontally from one rim to another in the center of the crotch region. The depth is then measured from that line to the base of the foam shell on the longitudinal axis. This depth ranges from about 0.5 to about 2.5 inches. The foam shell may be made of other suitable compositions which are soft and flexible and are liquid-impermeable.

The superstructure is comprised of hydrophobic, wet resilient, dry resilient fibers in web form. The web has a liquid pass-through rate of at least about 20 cc/second. The liquid pass-through rate is the rate at which a liquid can be poured on one surface of the web and substantially pass through the web. A fibrous web generally is formed from synthetic fibers such as polyethylene, polypropylene, polyester, polyamide fibers, bi-component fibers, copolymers thereof, mixtures thereof and the like. The fibers are placed in the web by known means, such as by carding to form a web which is then stabilized if needed. Stabilization may be achieved by heat-through bonding, adhesive bonding, point embossing with heat or adhesive (or both), needle punching, use of water jets and the like. The stabilizing process is selected according to the fibers used and the process used to form the web. Other suitable procedures for forming a web include air-laying, wet-laying, spun bonding, laying of melt-blown fibers, spread tow, and other known techniques. A typically suitable web has a dry bulk of at least about 10 cc/gm and a weight less than about 7 oz/yd$^2$. The superstructure is a primary contributor to the product's high transverse post-compression recovery.

To determine the transverse post-compression recovery a product sample of a determined width is immersed in 1.59% saline solution until substantially saturated. The saturated product is placed on a platen or base plate in between vise-like jaws. The jaws are brought together to reduce the width of the product by about 75% and held in the narrowing position for 30 seconds. The jaws are then released and the product allowed to recover for 30 seconds whereupon the degree of recovery of the initial width is measured. The recovered width expressed as a percentage of the initial width is the transverse post-compression recovery.

In a preferred embodiment, a fibrous web is corrugated and stabilized so as to prevent loss of corrugation when the fibrous web becomes wet. Corrugating or transverse folding of the web may be carried out by procedures such as that in U.S. Pat. No. 4,111,733. Generally, the web corrugations will range from about 3 to 6 or even 8 per inch of corrugated web, and the web thickness will be from about ¼ to about 3 inches, preferably from about ½ to about 1 inch thick. One method of stabilizing the corrugations in the web is accomplished by using an adhesive. The corrugated web is sprayed with the adhesive on one corrugated surface thereof, or if desired on both corrugated surfaces. The adhesive is cured and the web thus stabilized. Another method of stabilizing the web is by adding a small portion of fusible fibers to the web fibers before or after the web is made. These fusible fibers have a lower melting point than the remaining fibers and when the corrugated web is subjected to temperatures sufficient to melt the fusible fibers, light bonding is provided between the corrugations.

In one specific embodiment, a blend of staple polyester fibers with a minor portion of fusible fibers such as lower melt polyester fibers are carded to form a web. The web is subseguently lightly bonded by passing hot air through the fibers making the fusible fibers tacky so as to stick to each other and the staple fibers to provide the desired degree of integrity to the corrugated web structure.

Fibrous webs may be used in non-corrugated form as well. For instance, a high loft, low density, stable fibrous web may be placed in the shell and either adhered to the shell wall or provided with a facing covering the web to provide a satisfactory urinary pad. If the desired thickness is not available in the web, more than one layer of the web may be used but preferably the capillary pressure provided by each web layer increases as the layers are placed away from the facing. In an example with three layers of fibrous webs, the top layer, that is the layer closes to the open side of the shell, has the lowest capillary pressure, the mid layer has a higher capillary pressure than the first layer but a lower capillary pressure than the third and last layer. Hence, the liquid leaves the surface rapidly as it is drawn into the lower layers.

What appears to be only a small difference in capillary pressure is all that is required for one layer to attract and drain liquid from an adjacent layer. The force causing a liquid to enter a cylindrical capillary is expressed by the eguation:

$$P = \frac{(2v \cos \theta)}{r}$$

wherein the force is represented by the Capillary pressure and

P is the capillary pressure,
$v$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero) and also increases with narrower capillary radii so that narrower capillaries will draw liquid from wider ones.

In one embodiment of the present invention, hydrophobic fibers in a fibrous web form the superstructure, while at least a portion of the absorbent medium is a layer of hydrophilic fibers. Thus the hydrophilic fibrous (or particle) layer is generally comprised of fibers having a lower liquid-contact angle or wherein the layer is provided with a narrower capillary radii or both. Examples of hydrophilic fibers include rayon fibers, cellulosic fibers, or peat moss, or mixtures thereof, or acrylic fibers, or the like. A layer of hydrophilic fibers provides a suitable absorbent medium.

Cellulosic fibers, particularly, wood pulp fibers, generally are used to form the fluff or fibrous batt layer in conventional absorbent products such as disposable diapers, sanitary napkins, etc. Other cellulosic fibers that might be used are rayon fibers, cellulose acetate fibers, flax, hemp, jute, ramie, cotton, and the like. The fiber, or peat moss, or mixtures thereof are placed in such a way as to form a layer in which the particles are close to one another so as to promote wicking of liquid in the plane of the layer.

The hydrophilic fiber layer can be preformed and placed next to the hydrophobic fibrous layer or, the particles (fibers or peat moss or mixtures thereof) can be air-laid or wet-laid, or otherwise combined with the hydrophobic fibrous layer before any transverse folding or corrugating takes place.

A multiple layer structure may be corrugated or simply used in its multiple layer form.

Another material, though not preferred, suitable for making the superstructure is a foam. The foam should be slightly compressible, reasonably flexible, and must be able to maintain a void volume, i.e., hold liquid reasonably when wet. The foam needs to be in a form that allows liquid to enter the entire foam structure and at the same time has at least some collapse resistance sufficient to maintain the void volume of the foam. A foam-type structure which in its unaltered form that is not satisfactory is a sponge. Although a sponge does have the collapse resistance and has the necessary void volume, a sponge tends not to provide adequate impact capacity. In other words, the liquid upon initial contact is not immediately entrapped in the void volume space. However, if a sponge is chopped up into pieces or if holes are put into the sponge, so as to permit the liquid to enter a void space initially, the sponge will perform satisfactorily.

The foam may be placed in the shell in sheet form whereupon, if the sheet is sufficiently thick, only one is required, but if layered it is preferable that there be a capillary difference between the layers as discussed hereinbefore. The foam may be placed in the shell in chopped pieces or perhaps in the form of beads such as styrofoam beads. The foam may be thick and cast into the shell so as to form fit the shell. Suitable foams include polyurethane foams, polystyrene foams, and the like.

The superstructure is selected so as to provide sufficient void spaces to hold a normal liquid void and provide an impact capacity capable of receiving the liquid rapidly enough to prevent a run off. Also, the superstructure should be able to retain the liquid even under normal pressure such as that provided by the wearer of the pad when sitting down or moving the legs thereby slightly compressing the urinary pad until the absorbent medium can absorb substantially all the liquid.

One means of providing an increase in the liquid capacity of the product is the placement of superabsorbent in intimate contact with at least a portion of the superstructure.

The superabsorbent, present either on the fibers of a web or placed in the folds of a corrugated web, or otherwise associated with the spaces in the superstructure, is generally a water-insoluble, water-swellable polymeric substance capable of absorbing water in an amount which is at least 10 times the weight of the substance in its dry form. The superabsorbent is in the form of fibers, spheres particles, bits of film, globules, webs, film or the like, or may be applied in the form of a liquid monomer solution which is subsequently polymerized. The superabsorbent prepared by polymerization of a monomer solution placed on fibers in a web is most frequently in the form of globules and bits of film-like particles in the web structure.

One type of superabsorbent material provides particles or fibers which may be described chemically as having a backbone of natural or synthetic polymers with hydrophilic groups or polymers containing hydrophilic groups being chemically bonded to the backbone or an intimate mixture therewith. Included in this class of materials are such modified natural and regenerated polymers as polysaccharides including for example, cellulose and starch and regenerated cellulose which are modified by being carboxyalkylated, phosphonoalkylated, sulfoalkylated, or phosphorylated to render them highly hydrophilic. Such modified polymers may also be cross-linked to improve their water-insolubility.

These same polysaccharides may also serve, for example, as the backbone on to which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula:

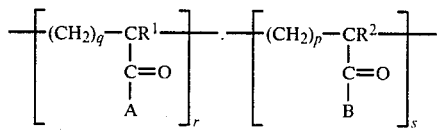

wherein A and B are selected from the group consisting of $-OR^3$, $-O$(alkali metal), $-OHNH_3$, $-NH_2$, wherein $R^1$, $R^2$, and $R^3$ are selected from the group consisting of hydrogen and alkylene having 1 to 4 or more carbon atoms wherein r is an integer having a value of 0 to about 5000 or more, s is an integer having a value of 0 to about 5000 or more, r plus s is at least 500, p is an integer having a value of 0 or 1, and q is an integer having a value of 1 to 4. The preferred hydrophilic chains are hydrolyzed polyacrylonitrile chains and copolymers of polyacrylamide and polysodium acrylate.

In addition to the modified natural and regenerated polymers, the hydrocolloid component may comprise wholly synthetic hydrophilic particles. Examples of those now known in the art are polyacrylonitrile fibers which may be modified by grafting moieties thereon such as polyvinylalcohol chains, polyvinyl alcohol itself, hydrophilic polyurethane, poly(alkyl phosphonates), partially hydrolyzed polyacrylamides (e.g., poly(N-N-dimethylacrylamide), sulfonated polystyrene, or a class of poly(alkyleneoxide). These highly hydrophilic synthetic polymers may be modified by other chemical treatments such as cross-linking or hydrolysis. Further examples known in the art are the non-ionic polymers such as polyoxyethylene, polyoxypropylene, and mixtures thereof which have been suitably cross-linked, either chemically or by irradiation. Still another more recent type is a derivative of isobutylene-maleic anhydride copolymer.

Hydrophilic polymers formed from water-soluble acrylate monomers, such as sodium, potassium, ammonium, (or a combination of cations), acrylate, may be placed on a fibrous web by spraying or otherwise placing a solution thereon, followed by polymerization and crosslinking, for example, by irradiation.

In addition, naturally occurring materials such as gums may be used. Examples of such suitable gums include guar gums, acacia gums, locust bean gums and the like.

The superabsorbent may be placed in the bottom of the shell prior to the placing of the superstructure in the shell or it may be a minor part of the superstructure. If the superstructure is a fibrous web having substantially uniform density throughout, the superabsorbent is best placed between the fibrous web and the inside surface of the shell. Another alternative method of placing superabsorbent on or within a fibrous web, is by spraying a monomer solution on the fibrous web or perhaps even saturating the web with a monomer solution followed by polymerization and cross-linking of the monomer. One typical way to polymerize the monomer is by use of irradiation. This places the superabsorbent substantially evenly throughout the fibrous web and affixes the superabsorbent in such a manner that the superabsorbent globules or particles are spaced apart to permit them to swell substantially to completion.

If the web is corrugated or transversely folded, superabsorbent can be placed within the folds provided it is sufficiently associated with the superstructure that the swelling of the superabsorbent can occur. If the web is a multiple layer web, it is desirable to associate the superabsorbent with the web having the highest capillary pressure. Another concept is the placement of superabsorbent in a pre-established situation, such as within a moisture-permeable bag such as a "tea bag", or a pocket, or the like. If the superabsorbent is in the form of granules, it may be desirable to moisten the granules and then fix them in place either on the web or in the foam or at the surface of the shell, which will be in contact with the superstructure.

In summation, the superstructure can be any structure which has at least a slight degree of compressibility, which allows liquid to enter the structure rapidly, that retains and subsequently allows draining of the liquid, and provides collapse resistance so that the liquid is not pressed out of the superstructure until the liquid is absorbed by the absorbent medium whereupon the superstructure is again available to receive more liquid.

The product of the present invention does not require a facing or cover but if no facing or covering is used, then it is necessary to secure the superstructure within the shell so that prior to or during use the superstructure does not separate itself from the shell. If, however, it is desirable to use a covering or facing, the covering or facing placed over the open side of the shell is liquid-permeable and is readily sealable to the outer rim of the shell so as to entrap the superstructure in the shell. Suitable coverings or facings include fabrics, nonwoven webs, perforated films, and the like. Preferably, the facing is a thermoplastic substance which can be heat sealed to the rim of the liquid-impermeable shell.

The product of the present invention is worn by the wearer in the crotch region, and for simplicity is secured to the underclothing of the wearer. Securement may be effected by adhesive lines or strips on the exterior of the shell or may simply secure itself to the underclothing by means of friction. If the product is to be secured by friction, a material for manufacturing the shell is selected which will provide sufficient friction or a material is coated on the exterior of the shell to provide such friction.

Examples for the preparation of the present invention are as follows. These examples are not intended to be limiting in any way and extensions and modifications thereof, without departure from the spirit and scope of the invention, will become apparent from these examples.

EXAMPLE I

A soft flexible shell is formed by thermoforming an ethylenevinyl acetate copolymer blend foam sheet. The shell has a length of 8 inches, a width at the widest point of 4⅜ inches, and a width at the central portion at its narrowest point of 3¾ inches. The shell is ⅞ inches deep at the center from a line extending across the center from the edge of each rim of the shell.

The superstructure and part of the absorbent medium placed in the shell consists of a two layer fibrous web which has been corrugated. The upper layer (which consists of 50 percent by weight of the web) is a blend of 75 parts of polyester staple fibers with 25 parts of polyester binder fibers. The average denier of the fibers is about 15. The second layer (also making up 50% of the web) is 40 parts acrylic fibers of 1.5 denier blended with 10 parts by weight of the same binder fibers used in the top layer. Each of the layers of the web are carded and one layer is placed upon the other. The two layer web structure is then corrugated and heat set at about 315° F. The corrugated two layer web is ⅜ inch high and has approximately 4.5 folds per inch of corrugation. The corrugated web has a weight of about 12 oz./yd$^2$.

The remaining portion of the absorbent medium is a blend of superabsorbent identified as 1OSH manufactured and sold by Mitsubishi Company, Tokyo, Japan, and mineral oil. Four parts of superabsorbent are mixed with one part of mineral oil. This blend is placed on the bottom fiber layer of the two layer web and between the folds to a depth of approximately ¼ to ½ inch. The amount of the blend added is approximately 1 gram of the superabsorbent-mineral oil blend per gram of two layer web structure.

A nonwoven fabric made from bicomponent fibers of polyester core and polyethylene sheath having a weight of about 0.5 oz./yd$^2$, is heat sealed to the rim of the shell to provide a facing or covering for the product.

The product is tested by adding 20 cc per second of simulated urine liquid. After the addition of the liquid, the product is left in its receiving position for 5 seconds and then is turned so that the corrugations, if present, are vertical. With a discharge of 100 cc (which would occur in 5 seconds), the retention of the product exhibited is 98 percent. With a discharge of 150 cc (in 7 seconds), the retention of the product is 85 percent. With a discharge of 200 cc (over a period of 10 seconds), the retention of the produot when turned vertically is 82 percent. The product exhibits a transverse post-compression recovery of at least 95%.

It becomes readily apparent from the above example that the present invention provides a highly satisfactory product for use by incontinent adults who are active people. It is truly surprising that a structure can be provided which will hold at least 80 percent of a 200 cc discharge of urine after merely 5 seconds contact time.

From the foregoing it will be observed that numerous variations and modifications may be effected without departing from the true spirit and scope of the novel concept of this invention.

I claim:

1. A disposable urinary pad comprising a liquid-impermeable substantially flexible relatively thin shell having a length from about 4 to about 12 inches, a width from about 2 to about 7 inches, and a depth from about 0.5 to about 2.5 inches;
   a superstructure placed in and substantially filling said shell, said superstructure consisting essentially of a fibrous web of hydrophobic, wet resilient, dry resilient fibers, said web allowing liquid to pass through the web at a rate of at least about 20 cc/second; and
   an absorbent medium in intimate contact with at least a portion of said superstructure and at least a portion of said shell,
   said pad having a transverse recovery when wet of at least about 80% following compression of up to 25% of its width wherein said superstructure is a primary contributor to said recovery.

2. The pad of claim 1 wherein said absorbent medium is comprised of superabsorbent material, hydrophilic fibers, a nonwoven web of hydrophilic fibers, wadding, tissue, peat moss, or mixtures thereof.

3. The pad of claim 1 wherein said shell is an ethylene-containing polymer foam shell having a thickness of about 1/64 inch to about ¼ inch.

4. The pad of claim 3 wherein said shell is a thermal formable substance.

5. The pad of claim 1 wherein said superstructure is comprised of a corrugated fibrous web.

6. The pad of claim 5 wherein said corrugated fibrous web is comprised of polyester fibers.

7. The pad of claim 1 wherein said absorbent medium is comprised of superabsorbent material.

8. The pad of claim 1 wherein said absorbent medium is comprised of loosely compacted wood pulp fibers.

9. The pad of claim 1 wherein said absorbent medium is comprised of superabsorbent material and hydrophilic fibers.

10. The pad of claim 1 wherein said superstructure and at least a part of said absorbent medium comprise a two layered fibrous web.

11. The pad of claim 10 wherein said superstructure is comprised of polyester fibers and said absorbent medium is comprised of acrylic fibers and superabsorbent material.

12. The pad of claim 11 wherein said polyester fibers and said acrylic fibers form a two layered web which is a corrugated web.

13. The pad of claim 11 wherein said superabsorbent material is comprised of polysodium acrylate.

14. The pad of claim 1 wherein said shell is a cross-linked polyethylene foam shell having a thickness from about 1/64 inch to about ¼ inch.

15. The pad of claim 1 wherein said shell has a depth from about 0.5 to about 2.5 inches.

16. The pad of claim 15 wherein said shell has a depth from about 0.5 to about 1.5 inches.

17. The pad of claim 1 wherein said shell has a boat-like shape.

18. The pad of claim 1 wherein the transverse post-compression recovery is at least about 90%.

19. The pad of claim 1 wherein said superstructure has a dry bulk of at least about 10 cc/gm and a weight less than about 7 oz/sq. yd.

20. A disposable urinary pad comprising a liquid-impermeable, substantially flexible, relatively thin shell having a length from about 4 to about 12 inches, a width from about 2 to about 7 inches, and a depth from about 0.5 to about 2.5 inches,
   a superstructure placed in and substantially filling said shell, said superstructure consisting essentially of a corrugated fibrous web of hydrophobic, wet resilient, dry resilient fibers, said web in its uncorrugated form, allowing liquid to pass through the web at a rate of at least about 20 cc/second; and an absorbent medium comprised of superabsorbent material, hydrophilic fibers, a nonwoven web of hydrophilic fibers, wadding, tissue, peat moss, or mixtures thereof, in intimate contact with at least a portion of said superstructure and at least a portion of said shell, said pad having a transverse recovery when wet of at least about 80% following compression of up to 25% of its width.

21. The pad of claim 20 wherein said corrugated fibrous web is comprised of polyester fibers.

22. The pad of claim 20 wherein said absorbent medium is comprised of superabsorbent material.

23. The pad of claim 20 wherein said absorbent medium is comprised of loosely compacted wood pulp fibers.

24. The pad of claim 20 wherein said absorbent medium is comprised of superabsorbent material and hydrophilic fibers.

25. The pad of claim 20 wherein said superstructure and at least a part of said absorbent medium comprise a two layered fibrous web.

26. The pad of claim 25 wherein said superstructure is comprised of polyester fibers and said absorbent medium is comprised of acrylic fibers and superabsorbent material.

27. The pad of claim 26 wherein said polyester fibers and said acrylic fibers form a two layered web which is a corrugated web.

28. The pad of claim 26 wherein said superabsorbent material is comprised of polysodium acrylate.

29. A disposable urinary pad comprising an ethylenevinyl acetate copolymer shell which is substantially flexible, relatively thin shell having a length from about 4 to about 12 inches, a width from about 2 to about 7 inches, and a depth from about 0.5 to about 2.5 inches, a superstructure placed in and substantially filling said shell, said superstructure consisting essentially of a corrugated polyester fiber web, said web allowing liquid to pass through the web at a rate of at least about 20 cc/second; and an absorbent medium in intimate contact with at least a portion of said superstructure and at least a portion of said shell, said absorbent medium comprising an acrylic fiber web and superabsorbent material, said pad having a transverse recovery when wet of at least about 90% following compression of up to 25% of its width.

30. The pad of claim 29 wherein said polyester fibers and said acrylic fibers form a two layered web which is a corrugated web.

* * * * *